United States Patent

Meconi et al.

Patent Number: 6,090,404
Date of Patent: Jul. 18, 2000

[54] ESTRADIOL PENETRATION ENHANCERS

[75] Inventors: Reinhold Meconi, Neuwied; Frank Seibertz, Bad Hönningen/Ariendorf, both of Germany

[73] Assignee: LTS Lohmann Therapie-Systeme GmbH, Neuwied, Germany

[21] Appl. No.: 08/682,511

[22] PCT Filed: Jan. 5, 1995

[86] PCT No.: PCT/EP95/00032

§ 371 Date: Oct. 11, 1996

§ 102(e) Date: Oct. 11, 1996

[87] PCT Pub. No.: WO95/19162

PCT Pub. Date: Jul. 20, 1995

[30] Foreign Application Priority Data

Jan. 13, 1994 [DE] Germany .............................. 44 00 770

[51] Int. Cl.⁷ ...................................................... A61F 13/02
[52] U.S. Cl. ............................................ 424/448; 424/449
[58] Field of Search ..................... 42/448, 449; 604/896, 604/897

[56] References Cited

U.S. PATENT DOCUMENTS

| | | | |
|---|---|---|---|
| 4,624,665 | 11/1986 | Nuwayser | 604/307 |
| 4,687,481 | 8/1987 | Nuwayser | 604/897 |
| 5,126,144 | 6/1992 | Jaeger et al. | 424/448 |
| 5,200,190 | 4/1993 | Azuma et al. | 424/443 |
| 5,248,676 | 9/1993 | Nakagawa et al. | 514/182 |
| 5,252,588 | 10/1993 | Azuma et al. | 514/317 |
| 5,393,529 | 2/1995 | Hoffmann et al. | 424/445 |
| 5,518,734 | 5/1996 | Stefano et al. | 424/448 |

FOREIGN PATENT DOCUMENTS

| | | |
|---|---|---|
| 0 072 251 | 2/1983 | European Pat. Off. . |
| 0 186 019 | 7/1986 | European Pat. Off. . |
| 0 275 716 | 7/1988 | European Pat. Off. . |
| 0 285 563 | 10/1988 | European Pat. Off. . |
| 0 328 806 | 8/1989 | European Pat. Off. . |
| 0 371 496 | 6/1990 | European Pat. Off. . |
| 0 430 491 | 6/1991 | European Pat. Off. . |
| 0 569 338 | 11/1993 | European Pat. Off. . |
| 2 006 969 | 10/1970 | Germany . |
| 3 205 258 | 9/1982 | Germany . |
| 3 743 946 | 3/1989 | Germany . |
| 3 843 239 | 2/1990 | Germany . |
| 3 933 460 | 4/1991 | Germany . |
| WO87/07138 | 12/1987 | WIPO . |

OTHER PUBLICATIONS

Banakar, Pharmaceutical Dissolution Testing, 1st Editionj, 1991, pp. 330–341 Marcel Dekker, Inc. New York, New York.

*Primary Examiner*—Jose' G. Dees
*Assistant Examiner*—Kathryne E. Shelborne
*Attorney, Agent, or Firm*—Wenderoth, Lind & Ponack, L.L.P.

[57] ABSTRACT

An active substance-containing patch for the controlled release of estradiol or its pharmaceutically acceptable derivatives alone or in combination with gestagens from a backing layer, an active substance-containing reservoir connected thereto and produced by using pressure sensitive adhesives and at least one penetration enhancer, and a removable protective layer is characterized by the fact that the penetration enhancer is selected from substances based on carboxylic acids.

11 Claims, No Drawings

ESTRADIOL PENETRATION ENHANCERS

This application is a 371 of PCT/EP95/00032 filed Jan. 5, 1995.

The present invention relates to an active substance-containing patch for the controlled release of estradiol or its pharmaceutically acceptable derivatives alone or in combination with gestagens to the human or animal skin by using pressure sensitive adhesives and at least one penetration enhancer. The present invention further relates to its use and to a process for its production.

BACKGROUND OF THE INVENTION

Estrogen-containing patches have been known for some time. However, they have the disadvantages that they either contain ethanol, or that there is the potential risk that the active substance recrystallizes in the course of time, or that they do not release estradiol in an amount sufficient for therapy.

It is known from DE-OS 32 05 258 and EP 0 285 563 to administer estradiol and ethanol at the same time in a patch formulation. However, the production of said patch is very expensive and the wearing comfort after application is low due to the lack of flexibility.

EP 0 285 563 describes a transdermal therapeutic system for the combined application of estrogens and gestagens. The reservoir comprises an active substance formulation, optionally a membrane, as well as ethanol used as percutaneous absorption improving agent. The active substance release is mainly controlled by the membrane. In the patch described therein, the adhesive has the mere function of fastening the patch to the skin. The fact that it can contribute to the control of the active substance release is not its main function, what is more, this is merely a side effect—probably not desired at all. The patch described there is a so-called "pouch patch" since the active substance preparation is present in a pouch consisting of an impermeable backing layer and a membrane having an adhesive layer. As a consequence of its complicated structure, the production of this patch is very expensive, since the individual components have to be manufactured separately and then joined to form a patch in an additional process step.

EP 0 275 716 describes a two-layer transdermal therapeutic system for the simultaneous administration of one or several estrogens dissolved or microdispersed in the polymeric layer. In addition to the active agents, the adhesive layer comprises substances improving the transdermal absorption. Polymeric and adhesive layer may consist of polyacrylates, silicones, or polyisobutylenes.

EP 0 072 251 describes a flexible, moisture-absorbing medical bandage. The substrate attached to the flexible backing layer consists of a hydrophilic matrix based on hydrophilic, high-molecular polysaccharides and/or polyacrylic acid, polyacrylamide, ethylene-vinyl-acetate-copolymers, and other polymers, as well as of a liquid phase based on a solution or emulsion of carbohydrate, proteins, and polyhydric alcohols, as well as different active substances, amongst others hormones. An essential feature of this invention is the hygroscopic adhesive.

EP 0 328 806 describes a membrane-free, transdermal therapeutic system whose matrix consists of a polyacrylate adhesive, a solvent, a polyoxyethylene ester as penetration enhancer, and estrogens, the derivatives and combinations thereof.

WO 87/07 138 describes an estradiol patch based on a backing layer, an active substance-containing matrix, and a pressure sensitive adhesive covered with a removable protective layer. The production of the matrix and the adhesive is effected in technologically very expensive operations by homogenizing, degassing, coating, drying and separating. According to an embodiment, the backing layer must be coated with a pressure sensitive adhesive, involving another operational step. The individual parts are joined together in a separate step. For this reason, the manufacture of this patch is very expensive and complicated.

U.S. Pat. No. 4,624,665 describes systems containing the active substance in micro-encapsulated form in the reservoir. The reservoir is embedded between a backing layer and a membrane. The outer edge of the system is provided with a pressure sensitive adhesive. The structure and the production of this system is very complicated, since the active substance must be micro-encapsulated and homogeneously distributed in a liquid phase which is then embedded between backing layer and membrane in additional process steps. Additionally, the system must then be provided with an adhesive edge and covered with a protective layer.

Additionally, EP 0 186 019 describes active substance patches in which water-swellable polymers are added to a rubber-adhesive-resin mass and from which estradiol can be released. It turned out, however, that the estradiol release from these active substance patches is too low and does not meet the therapeutic requirements.

DE-OS 20 06 969 describes a patch or a pressure sensitive adhesive bandage having systemic action, in which contraceptive substances are incorporated into the adhesive component or adhesive film. The adhesive film may consist of an acrylate.

DE-OS 39 33 460 describes an estrogen-containing active substance patch based on homo and/or copolymers having at least one derivative of the acrylic acid or with methacrylic acid in combination with water-swellable substances.

EP 0 430 491 describes a transdermal therapeutic system comprising components intensifying the penetration of estradiol. These include unsaturated fatty acids, their alkyl esters and glycerol or alkanediols, such as propanediol. This formulation has the disadvantages that the unsaturated fatty acids are sensitive to oxidation and are thus subject to a chemical modification; additionally, propanediol evaporates in an uncontrolled manner during the drying process so that an active substance-containing patch which meets the required constant composition cannot be manufactured.

Also, the transdermal system described in EP 0 371 496 has the disadvantage that it comprises oleic acid as penetration enhancer, which is sensitive to oxidation and therefore does not allow the production of a stable system whose properties do not change during storage.

EP 0 569 338 describes a patch for the transdermal administration of estradiol by using penetration enhancers. These include saturated and unsaturated fatty acids and propylene glycol. The unsaturated fatty acids have the disadvantage that they are sensitive to oxidation, and that propylene glycol evaporates in an uncontrolled manner during the drying process. For this reason, an estradiol-containing patch having the required constant composition which does not change during storage cannot be manufactured.

Additionally, it turned out that pressure sensitive adhesive transdermal therapeutic matrix systems comprising the active substance in a partially or completely dissolved form do not release estradiol in the amount required for a therapy. There have been attempts of eliminating this drawback by enlarging the surface of the active substance patches.

However, this results in the fact that the patches partially peel off during the application period. Thus, the all-over contact to the skin which is required for the therapy is no longer ensured, and the active substance amount penetrating through the skin varies inadmissibly. For this reason, a therapy with a constant active substance administration cannot be ensured.

DESCRIPTION OF THE INVENTION

Accordingly, it is the object of the present invention to avoid the above-mentioned disadvantages and to provide an estrogen-containing patch releasing the active substance in a sufficient amount and avoiding the drawback of an unacceptable patch size.

Most surprisingly, it turned out that the object is achieved by means of an active substance-containing patch for the controlled release of estradiol or its pharmaceutically acceptable derivatives alone or combined with gestagens, which consists of a backing layer, an active substance-containing reservoir which is connected thereto and has been manufactured by using pressure sensitive adhesives, and a removable protective layer, with the pressure sensitive adhesive comprising at least one penetration enhancer of the group of substances based on carboxylic acids.

The substances based on carboxylic acids include glycollic acid, malic acid, lactic acid, tartaric acid, citric acid, mandelic acid, 2-hydroxycinnamic add, 3-hydroxycinnamic-acid, trans-4-methoxycinnamic acid, 2-hydroxyoctanoic acid, tropic acid, gallic acid, shikimic acid, benzilic acid, benzene-1,2,4-tricarboxylic acid, dimethyl-3-oxoglutarate, 3-methyl-2-oxo-valerianic acid, 4-methyl-2-oxo-valerianic acid, 2-oxoglutaric acid, pyruvic acid, 4-aminobutyric acid, 6-aminohexanoic acid, 11-aminoundecanoic acid, asparaginic acid, 2-aminobenzoic acid, 3-aminobenzoic acid, 4-aminobenzoic acid, 4-amino-2-salicylic acid, 3-phenylpropionic acid, 2-phenylbutyric acid, 4-phenylbutyric acid, succinic acid, glutaric acid, 3,3-dimethylglutaric acid, adipic acid, pimelic acid, azelainic acid, sebacic acid, trans-2-dodecenedioic acid, tridecanedioic acid, tetradecanedioic acid, pentadecanedioic acid, diglycollic acid, piperidine-4-carboxylic acid, pyrazine-2-carboxylic acid, pyrazine-2,3-dicarboxylic acid, pyridine-2-carboxylic acid, and nicotinic acid, pimelic acid monomethyl ester, malonic acid diamide, adipic acid diamide, succinic acid diamide, pyrazine-2-carboxamide.

The portion of penetration enhancers based on carboxylic acids amounts to 0.01–20%-wt.

In an embodiment of the present invention, components of the estradiol-containing pressure sensitive adhesive may be polymers selected from the group consisting of styrene-butadiene-styrene block copolymers, styrene-isoprene-styrene block copolymers, styrene-ethylene-butylene-styrene block copolymers, polyisobutylenes, ethylene-vinyl acetate copolymers, polyvinyl pyrrolidone, cellulose derivatives, polycaprolactams, polycaprolactones, ethylene-ethyl-acrylate copolymer, polyvinylether, polyvinylacetals, polyvinylacetates, butyl-rubbers, acrylonitrile-butadiene copolymers, polyethylene glycols, and polymers based on acrylic acid and methacrylic acid derivatives. These polymers are comprised in the estradiol-containing adhesive mass in a concentration of at least 6%-wt.

The active substance patch may comprise tackifying resins in the concentration of 5–94%-wt. These are known to those skilled in the art and are described in U.S. Pat. No. 5,126,144.

The active substance patch comprises in the reservoir, estradiol or its pharmaceutically acceptable derivatives alone or in combination with gestagens in a concentration totaling 2–15%-wt., that is in a molar ratio of estradiol or its pharmaceutically acceptable derivatives to gestagens of 1:1 to 1:10.

The estradiol-containing reservoir may comprise at least one inactive ingredient of the group including dyes, fillers, anti-ageing agents, plasticizers, and antioxidants. These inactive ingredients are known to the skilled artisan and are described, for example, in DE 37 43 946. The estradiol-containing reservoir normally comprises inactive ingredients in a portion of up to 5%-wt.

The active substance patch may consist of one single or of several layers. The thickness of the active substance-containing reservoir may amount to 0.02–1.0 mm.

The materials for the impermeable backing layer and the removable protective layer are also known to the expert (e.g., DE 38 43 239).

The estradiol-containing reservoir may be formed from a solution, dispersion, or from a melt.

Additionally, the reservoir may consist of several layers.

In case the reservoir should not have a sufficient self-tackiness to the skin, it can be provided with a pressure sensitive adhesive layer or with a pressure sensitive adhesive edge. This ensures adhesion of the transdermal patch to the skin over the whole application period.

A particularly preferred structure of the transdermal estradiol-containing patch is the matrix system; here, as is generally known, the matrix controls the active substance release which follows the √t-law according to Higuchi. However, this does not mean that the membrane system may not be expedient in particular cases, too. In this case, a membrane controlling the active substance release is provided between the reservoir and the pressure sensitive adhesive layer.

The present invention will be illustrated by the following examples.

EXAMPLE 1

66.7 g triethylene glycol ester of hydrogenated colophony (Staybelite Ester 3E of Hercules)

8.9 g glycerol ester of hydrogenated colophony (Staybelite Ester 10E of Hercules)

8.9 g ethyl cellulose and 1 g butyl hydroxyanisole are homogenized by stirring at 165° C. for about 1½ hours. Subsequently, 10.0 g DL-malic acid is added and stirring is effected for about 2 hours. Then 2.5 g estradiol is added and stirring is carried out for another 2 hours at 165° C.

The active substance-containing adhesive mass thus obtained is coated in a hotmelt-coating line (nozzle coating system) onto a removable protective layer (Hostaphan RN 100, coated on one side with silicone, Kalle) in such a manner that an active substance-containing reservoir results that has a mass per unit area of 80 g/m$^2$. The impermeable backing layer (polyester film, thickness 15 μm) is laminated on this reservoir. Afterwards active substances patches having a size of 16 cm$^2$ are punched.

Analysis:

The active substance release of the transdermal patches of a size of 16 cm$^2$ is determined according to the Rotating-Bottle-method described in USP XXII in 0.9% saline at 37° C.

To measure the mice skin penetration, the skin of hairless mice is clamped into the Franz-cell. An estradiol-containing patch having an area of 2.54 cm² is glued on the skin, and the active substance release at 37° C. (acceptor medium: 0.9% saline) is measured (literature: Umesh V. Banakar Pharmaceutical dissolution testing, 1st edition, 1991).

The results are shown in Table 1.

TABLE 1

Results of Analysis

| Example | estradiol content µg/16 cm² | in vitro release µg/16 cm² · 4 h | penetration through skin of mice µg/16 cm² · 24 h |
|---|---|---|---|
| 1 | 2120 | 367 | 114 |
| acc. to DE 39 33 460 | 3200 | 1080 | 96 |

*48-hour-value minus 24-hour-value

The Table shows that a clearly improved penetration through the mice skin is obtained, as is proved by the comparative example of DE 39 33 460.

What is claimed is:

1. An active substance-containing patch for the controlled release of estradiol or a pharmaceutically acceptable derivative thereof, alone or in combination with a gestagen, said patch comprising (1) a backing layer, (2) an active substance-containing reservoir connected thereto and which is produced using pressure sensitive adhesives and at least one penetration enhancer, and (3) a removable protective layer, wherein the penetration enhancer is based on polyfunctional carboxylic acids, and is selected from the group consisting of glycollic acid, mandelic acid, 2-hydroxycinnamic acid, 3-hydroxycinnamic acid, trans-4-methoxycinnamic acid, 2-hydroxyoctanoic acid, tropic acid, gallic acid, shikimic acid, benzylic acid, benzene-1,2,4-tricarboxylic acid, dimethyl-3-oxoglutarate, 3-methyl-2-oxo-valerianic acid, 4-methyl-2-oxo-valerianic acid, 2-oxoglutaric acid, pyruvic acid, 4-aminobutyric acid, 6-amino-hexanoic acid, 11-aminoundecanoic acid, asparaginic acid, 2-aminobenzoic acid, 3-aminobenzoic acid, 4-aminobenzoic acid, 4-amino-2-salicylic acid, 3-phenylpropionic acid, 2-phenylbutyric acid, 4-phenylbutyric acid, trans-2-dodecanedioic acid, tridecanedioic acid, tetradecanedioic acid, pentadecanedioic acid, diglycollic acid, piperidine-4-carboxylic acid, pyrazine-2-carboxylic acid, pyrazine-2,3-dicarboxylic acid, pyridine-2-carboxylic acid, nicotinic acid, pimelic acid monomethyl ester, malonic acid diamide, adipic acid diamide, pyrazine-2-carboxamide and succinic acid diamide.

2. The active substance patch according to claim 1, wherein the reservoir comprises the penetration enhancer in a concentration of 0.01–20%-wt.

3. The active substance patch according to claim 1, wherein the pressure sensitive adhesive comprises polymers in a concentration of at least 6%-wt.

4. The active substance patch according to claim 1, wherein the pressure sensitive adhesive comprises tackifying resins in the concentration of 5–94%-wt.

5. The active substance patch according to claim 1, wherein the reservoir comprises the active substance in concentration totaling 2–15%-wt.

6. The active substance patch according to claim 1, wherein the administration is in combination with a gestagen and the molar ratio of estradiol or a pharmaceutically acceptable derivative thereof to gestagen is 1:1 to 1:10.

7. The active substance patch according to claim 1, wherein the reservoir comprises up to 5%-wt. of inactive ingredients of the group consisting of dyes, fillers, antiageing agents and plasticizers with antioxidants.

8. The active substance patch according to claim 1, wherein the reservoir is formed of several layers.

9. The active substance patch according to claim 1, wherein the thickness of the reservoir is in the range of 0.02–1.0 mm.

10. The active substance patch according to claim 1, wherein the reservoir is provided with an additional pressure sensitive adhesive layer or with a pressure sensitive adhesive edge.

11. A method for the administration of estradiol or a pharmaceutically acceptable derivative thereof to a human or an animal in need of such treatment which comprises applying to the skin of such human or animal an active substance-containing patch as defined in claim 1.

* * * * *